(12) United States Patent
Oka et al.

(10) Patent No.: US 6,566,534 B2
(45) Date of Patent: May 20, 2003

(54) PROCESSES FOR THE PREPARATION OF AZIRIDINE COMPOUNDS AND VAPOR-PHASE REACTION PROCESSES

(75) Inventors: Yoshihisa Oka, Kanagawa-ken (JP); Kenichi Takematsu, Kanagawa-ken (JP)

(73) Assignee: Nippon Shokubai Co., Ltd., Osaka (JP)

( * ) Notice: Subject to any disclaimer, the term of this patent is extended or adjusted under 35 U.S.C. 154(b) by 0 days.

(21) Appl. No.: 09/984,466

(22) Filed: Oct. 30, 2001

(65) Prior Publication Data

US 2002/0055642 A1 May 9, 2002

(30) Foreign Application Priority Data

Nov. 6, 2000 (JP) ........................................ 2000-336902

(51) Int. Cl.⁷ ............................................. C07D 203/04
(52) U.S. Cl. ....................................................... 548/954
(58) Field of Search .......................................... 548/954

(56) References Cited

U.S. PATENT DOCUMENTS 4,966,980 A  * 10/1990  Kamei et al. ................ 548/954

FOREIGN PATENT DOCUMENTS

| JP | 217659/92 | 8/1992 |
| JP | 55498/93  | 8/1993 |
| JP | 88353/95  | 9/1995 |

* cited by examiner

Primary Examiner—Alan L. Rotman
Assistant Examiner—Andrea D. Small
(74) Attorney, Agent, or Firm—Sherman & Shalloway

(57) ABSTRACT

In order to carry out various vapor-phase reactions (e.g., the preparation of aziridine compounds by a vapor-phase intramolecular dehydration reaction) with industrial advantages, there is provided a process which can effectively prevent the adhesion of tarry matter to piping and the like. This process is applicable, for example, to the preparation of aziridine compounds by using a reactor for carrying out the vapor-phase intramolecular dehydration reaction of an alkanolamine, a collection column for collecting an aziridine compound present in the reaction gas, and a distillation column for distilling the collector liquid to obtain a purified aziridine compound, and is characterized in that at least the piping section extending from the outlet of the reactor to the inlet of the collection column is maintained at a temperature which is not lower than 200° C., or in that the reaction gas is brought into contact with a collector prior to its introduction into the collection column.

5 Claims, 1 Drawing Sheet

PROCESSES FOR THE PREPARATION OF AZIRIDINE COMPOUNDS AND VAPOR-PHASE REACTION PROCESSES

TECHNICAL FIELD TO WHICH THE INVENTION BELONGS

This invention relates to vapor-phase reaction processes and, in particular, vapor-phase processes for the preparation of aziridine compounds. More particularly, it relates to processes in which vapor-phase reactions, especially vapor-phase reactions for the preparation of aziridine compounds from alkanolamines, can be carried out with industrial advantages.

PRIOR ART

Conventionally, aziridine compounds have been prepared according to a liquid-phase process, i.e., a process wherein a sulfuric ester of monoethanolamine is treated with a concentrated alkaline solution to form ethyleneimine. However, this process has many disadvantages from an industrial point of view. For example, this process involves high production costs because large amounts of sulfuric acid and alkali are required as secondary raw materials, and this process yields inorganic salts of less utility value as by-products.

In recent years, therefore, a vapor-phase process wherein an aziridine compound is directly prepared by subjecting an alkanolamine to a vapor-phase intramolecular dehydration reaction in the presence of a catalyst (the vapor-phase intramolecular dehydration reaction in the presence of a catalyst may hereinafter be referred to briefly as the "dehydration reaction") is being employed because it requires no secondary raw material and is hence advantageous from the viewpoint of cost. As to the preparation of aziridine compounds by a vapor-phase reaction, a variety of processes have been proposed.

For example, Japanese Patent Laid-Open No. 217659/'92 discloses a process comprising a reaction step for forming an aziridine compound by the dehydration reaction of an alkanolamine, a collection step for collecting the aziridine compound so formed by bringing the reaction mixture containing the aziridine compound into contact with the same alkanolamine as used in the reaction step (i.e., a collector), a purification step for introducing the collector liquid containing the aziridine compound (hereinafter referred to briefly as the "collector liquid") into a purification column and purifying the aziridine compound, and a recovery step for recovering the alkanolamine by distilling the bottoms withdrawn from the purification column in the presence of water.

Japanese Patent Publication No. 55498/'93 discloses a process wherein the dehydration reaction of an alkanolamine is carried out in the absence of any diluent gas or in the presence of a small amount of a diluent gas. According to this process, an aziridine compound can be obtained by cooling the reaction gas so as to condense it, and introducing the resulting condensate directly to a distillation step, instead of subjecting the reaction gas to a collection step. Alternatively, this process may include a collection step. In this case, it is said that the amount of collector used can be reduced.

Moreover, Japanese Patent Publication No. 88353/'95 discloses a process wherein, after the dehydration reaction of an alkanolamine, the resulting aziridine compound is collected by bringing the reaction gas into contact with a collector comprising an amine compound or a solution thereof. More specifically, this process comprises cooling the reaction gas, introducing the reaction gas into a collection column where the aziridine compound is collected by contact with a collector, and then introducing the collector liquid into a distillation column where it is distilled to obtain the aziridine compound.

As described above, generally known vapor-phase processes for the preparation of aziridine compounds from alkanolamines include one comprising a reaction step for forming an aziridine compound by the dehydration reaction of an alkanolamine, a collection step for collecting the aziridine compound present in the resulting reaction gas, and a purification step for distilling the collector liquid containing the aziridine compound to obtain an aziridine compound product; and one comprising the reaction step and the purification step and requiring no collection step. Moreover, as described in the aforementioned patents, it is common practice to cool the reaction gas resulting from the reaction step by means of a heat exchanger or the like and then feed it to the collection step or the purification step. More specifically, the reaction gas is cooled to $-10°$ C. or $100°$ C. and then fed to a collection column in the process of Japanese Patent Laid-Open No. 217659/'92; the reaction gas is cooled to $-10°$ C. and then fed to a distillation column in the process of Japanese Patent Publication No. 55498/'93; and the reaction gas is cooled to $110°$ C. and then fed to a collection column in the process of Japanese Patent Publication No. 88353/'95.

Problems to be Solved by the Invention

However, when an aziridine compound is prepared on an industrial scale, or example, by using a reactor (or reaction column), a collection column and a distillation column, tarry matter adheres to the equipment section extending from the outlet of the catalyst bed within the reactor to the collection column, particularly to the inside of a heat exchanger installed before the collection column for the purpose of cooling, or cooling to condense, the reaction gas and to the inner wall of the pipe extending from the heat exchanger to the collection column When such tarry matter adheres to the inside of the heat exchanger and the inner wall of the piping, various problems arise. That is, (1) an increase in pressure loss is caused to increase the amount of energy required for the vaporization of the alkanolamine raw material fed to the reactor; (2) it becomes necessary to shut down the plant and wash off the tarry matter; and (3) the piping may become clogged.

The above-described problems also arise unavoidably when various vapor-phase reactions, such as vapor-phase intramolecular dehydration reactions and vapor-phase intramolecular dealcoholization reactions, are carried out.

An object of the present invention is to solve the above-described problems of the prior art by providing a process for preparing aziridine compounds with industrial advantages by effectively preventing the adhesion of tarry matter to piping and the like.

Another object of the present invention is to provide a process for carrying out various vapor-phase reactions, such as vapor-phase intramolecular dehydration reactions and vapor-phase intramolecular dealcoholization reactions, with industrial advantages by effectively preventing the adhesion of tarry matter to piping and the like.

Means for Solving the Problems

According to investigations conducted by the present inventors, it has been found that the adhesion of tarry matter can be effectively prevented (1) by maintaining at least the piping section extending from the outlet of the reactor to the inlet of the collection column at a temperature which is not lower than 200° C., or (2) by bringing the reaction gas emerging from the outlet of the catalyst bed within the reactor into contact with the same collector as used in the collection column, preferably in the neighborhood of the outlet of the catalyst bed. The present invention has been completed on the basis of this finding.

Thus, the present invention provides a process for the preparation of aziridine compounds which comprises the step of introducing an alkanolamine into a reactor and forming an aziridine compound by the vapor-phase intramolecular dehydration reaction of the alkanolamine in the presence of a catalyst, and the step of introducing the reaction gas containing the aziridine compound so formed into a collection column and collecting the aziridine compound by contact with a collector, the process being characterized in that at least the piping section extending from the outlet of the reactor to the inlet of the collection column is maintained at a temperature which is not lower than 200° C.

Moreover, the present invention also provides a process for the preparation of aziridine compounds which comprises the step of introducing an alkanolamine into a reactor and forming an aziridine compound by the vapor-phase intramolecular dehydration reaction of the alkanolamine in the presence of a catalyst, and the step of introducing the reaction gas containing the aziridine compound so formed into a collection column and collecting the aziridine compound by contact with a collector, the process being characterized in that the reaction gas is brought into contact with a collector prior to its introduction into the collection column.

Furthermore, the present invention also provides a process for the preparation of aziridine compounds which comprises the step of introducing an alkanolamine into a reactor and forming an aziridine compound by the vapor-phase intramolecular dehydration reaction of the alkanolamine in the presence of a catalyst, the step of cooling the reaction gas containing the aziridine compound so formed by means of a cooler so as to condense the reaction gas, and the step of introducing the resulting condensate into a distillation column and distilling it therein to obtain the aziridine compound, the process being characterized in that the reaction gas is brought into contact with a collector prior to its introduction into the cooler.

In addition, the present invention also provides a vapor-phase reaction process comprising a vapor-phase reaction step and a collection step for collecting a desired product present in the reaction gas, or a vapor-phase reaction process comprising a vapor-phase reaction step, a cooling step for condensing the reaction gas, and a distillation step for distilling the resulting condensate, the process being characterized in that at least the piping section extending from the outlet of the reactor to the inlet of the collection column is maintained at a temperature which is not lower than 200° C., or in that the reaction gas is brought into contact with a collector prior to its introduction into the collection column or the cooler.

The reason why the processes of the present invention can effectively prevent the adhesion of tarry matter to piping and the like has not been fully elucidated as yet. However, the present inventors have theorized on the effects of the present invention as described below, though they do not wish to be bound by any theory. (1) As described in the aforementioned patents, the reaction gas contains carbonyl compounds and various amines (e.g., piperazine) as by-products. It is known that, among these by-products, carbonyl compounds react with the desired product (i.e., the aziridine compound) to form adducts. In conventional processes in which the reaction gas is cooled to 100° C. or so by means of a heat exchanger and then introduced into a collection column, these adducts condense within the heat exchanger or in the pipe connecting the heat exchanger with the collection column, and grow to form tarry matter. (2) Accordingly, if the piping section extending from the outlet of the reactor to the inlet of the collection column is maintained at a temperature which is not lower than 200° C., or if the reaction gas is brought into contact with the same collector as used in the collection column prior to the condensation and growth of the adducts contained therein (i.e., immediately after the reaction gas emerges from the outlet of the catalyst bed within the reactor and preferably in the neighborhood of the outlet of the catalyst bed) so as to incorporate the adducts into the collector, the condensation and growth of the adducts and hence the adhesion of tarry matter can be effectively prevented.

EMBODIMENTS OF THE INVENTION

The alkanolamine used as the raw material in the present invention is a compound represented by the general formula (1):

wherein R is hydrogen, methyl or ethyl X is hydroxyl or amino, and Y is amino when X is hydroxyl or hydroxyl when X is amino. Typical examples of this alkanolamine include monoethanolamine, isopropanolamine, 2-amino-1-propanol-1-amino-2-butanol and 2-amino-1-butanol.

The aziridine compound is a compound which is obtained by the dehydration reaction of the above-described alkanolamine and represented by the general formula (2):

wherein R has the same meaning as defined for the general formula (1). Typical examples of this aziridine compound include ethyleneimine, 2-methylethyleneimine and 2-ethylethyleneimine.

No particular limitation is placed on the process for preparing an aziridine compound by the dehydration reaction of an alkanolamine, and any of commonly known processes may be employed. Specifically, there may be employed, for example, a process comprising a reaction step for feeding a vaporized alkanolamine to a reactor where an aziridine compound is formed by the dehydration reaction of the alkanolamine, a collection step for feeding the reaction gas emerging from the reactor to a collection column where the aziridine compound is collected from the reaction gas, and a purification step for feeding the collector liquid to a distillation column where it is distilled to obtain an aziridine compound product; or a process comprising the same reaction step as described above, a condensation step for cooling the reaction gas emerging from the reactor so as to condense it, and a purification step for feeding the resulting condensate to a distiller where it is distilled to obtain an aziridine compound product. For the details of these processes, reference may be made to the aforementioned patents.

As the reactor, there may be used any of the reactors which are commonly used for the dehydration reaction of alkanolamines. When the dehydration reaction is carried out in the reactor, the temperature is usually in the range of 300 to 500° C. and preferably 350 to 450° C. The pressure may be atmospheric, reduced or elevated. In the case of reduced pressure, it may be in the range of 13 to 667 hPa (10 to 500 mmHg). The space velocity is usually in the range of 10 to 20,000 $h^{-1}$ and preferably 50 to 5,000 $h^{-1}$ (STP). Under reduced pressure, it is in the range of 50 to 2,000 $h^{-1}$ (STP). No particular limitation is placed on the type of the catalyst used for the dehydration reaction, and there may be used any of various commonly used catalysts including, for example, those described in European Patent Laid-Open Nos. 227461, 228898 and 230776.

As the collection column, there may be used a packed tower, a plate tower, a multitubular tower, a spray tower, a wetted wall tower or a combination thereof. As the collector, there may be used a member suitably selected from among the collectors which are commonly used for the collection of aziridine compounds. Although the same alkanolamine as that used as the raw material or an aqueous solution thereof may be used, it is convenient and economical to utilize the condensate of the reaction product. For example, after the liquid accumulated at the bottom of the collection column is passed through an external heat exchanger to deprive the liquid of sensible heat and heat of condensation, a portion of the liquid may be used as the collector. In this case, some of the raw material may be added thereto.

As the distillation column, there may be used any type of distillation column, such as a packed tower or a plate tower. The distillation process may be a continuous process or a batch process, and may be carried out under any of atmospheric, reduced and elevated pressures. The aziridine compound is discharged from the top of the distillation column and further purified, if necessary, to obtain an aziridine compound product. On the other hand, the bottoms including unreacted alkanolamine and by-products (e.g., produced water, Schiff bases, ketimines and piperazines) are withdrawn from the bottom of the distillation column. These bottoms are usually fed to a recovery column, where the alkanolamine is recovered. For the details of this recovery step, reference may be made to the aforementioned Japanese Patent Laid-Open No. 217659/'92.

As the cooler, a heat exchanger is usually used.

One feature of the present invention is [I] that, when an aziridine compound is prepared from an alkanolamine in the vapor phase according to a process comprising a reaction step, a collection step and a purification step, the adhesion of tarry matter to the piping section extending from the outlet of the reactor to the inlet of the collection column, and to other sections can be prevented (A) by maintaining at least the piping section extending from the outlet of the reactor to the inlet of the collection column at a temperature which is not lower than 200° C., or (B) by bringing the reaction gas into contact with a collector prior to its introduction into the collection column, preferably in the neighborhood of the outlet of the catalyst bed within the reactor. Another feature of the present invention is [II] that, when an aziridine compound is prepared according to a process comprising a reaction step, a condensation step and a purification step and requiring no collection step, the adhesion of tarry matter to the piping section extending from the outlet of the reactor to the cooler, the inside of the cooler, and other sections can be prevented (C) by bringing the reaction gas into contact with a collector prior to its introduction into the cooler, preferably in the neighborhood of the outlet of the catalyst bed within the reactor.

In the processes (A) and (B), the term "piping section" means not only the pipe connecting the outlet of the reactor with the inlet of the collection column, but also the cooler (e.g., heat exchanger) optionally installed before the collection column.

In the process (A), at least the piping section extending from the outlet of the reactor to the inlet of the collection column is maintained at a temperature which is not lower than 200° C. This may be accomplished by providing the piping section with a commonly used heating means (e.g., a heater) and heating the piping section therewith. As used herein, the temperature of the piping section refers to the temperature of the outer wall of the piping section. The piping section is usually maintained at a temperature in the range of 200 to 500° C. and preferably 300 to 400° C. If the temperature of the piping section is excessively high, the decomposition and combustion of the aziridine compound present in the reaction gas will occur to cause such problems as a reduction in yield.

Moreover, the section extending from the outlet of the catalyst bed within the reactor to the outlet of the reactor may also be heated (for example, by external heating) so as to minimize a reduction in the temperature of the reaction gas. This makes it possible to prevent the adhesion of tarry matter more effectively.

Furthermore, the adhesion of tarry matter can be more effectively prevented by bringing the reaction gas into contact with a collector prior to its introduction into the collection column, preferably in the neighborhood of the outlet of the catalyst bed within the reactor. The collector used for this purpose is usually the same as that used in the collection step.

Since a relatively hot reaction gas is fed to the collection column in the process (A), the degree of collection of the aziridine compound in the collection column is lower as compared with the conventional techniques in which the reaction gas is introduced into the collection column after being condensed or cooled to 100° C. or so. Consequently, it is preferable to cool, or cool to condense, the gas discharged from the collection column, introduce the gas into a second collection column, and thereby recover the aziridine compound. In this case, the pipe extending from the collection column to the cooler, the cooler, and the pipe extending from the cooler to the second collection column will not suffer from the adhesion of tarry matter. In addition, as shown in the flow sheet of FIG. 1 which will be given later, it is also possible to recover the aziridine compound by storing the collector liquid from collection column 103 and the condensate from cooler 104 in a storage tank 105 and introducing the gas discharged from storage tank 105 into second collection column 106.

In the process (B), it is preferable to bring the reaction gas into contact with the collector in the neighborhood of the outlet of the catalyst bed within the reactor, because this makes it possible to prevent the adhesion of tarry matter more effectively. The collector used for this purpose is usually the same as that used in the collection step. In the process (B), it is unnecessary to heat the piping section and thereby maintain its temperature as dictated in the process (A).

Also in the process (C), it is preferable to bring the reaction gas into contact with the collector in the neighborhood of the outlet of the catalyst bed within the reactor, because this makes it possible to prevent the adhesion of tarry matter more effectively. The collector used for this purpose is usually the same as that used in the collection step. For further information on the conditions of the reaction step and the like, reference may be made to Japanese Patent Publication No. 55498/'93.

BRIEF DESCRIPTION OF DRAWINGS

In the accompanying drawings.

Figure 1:
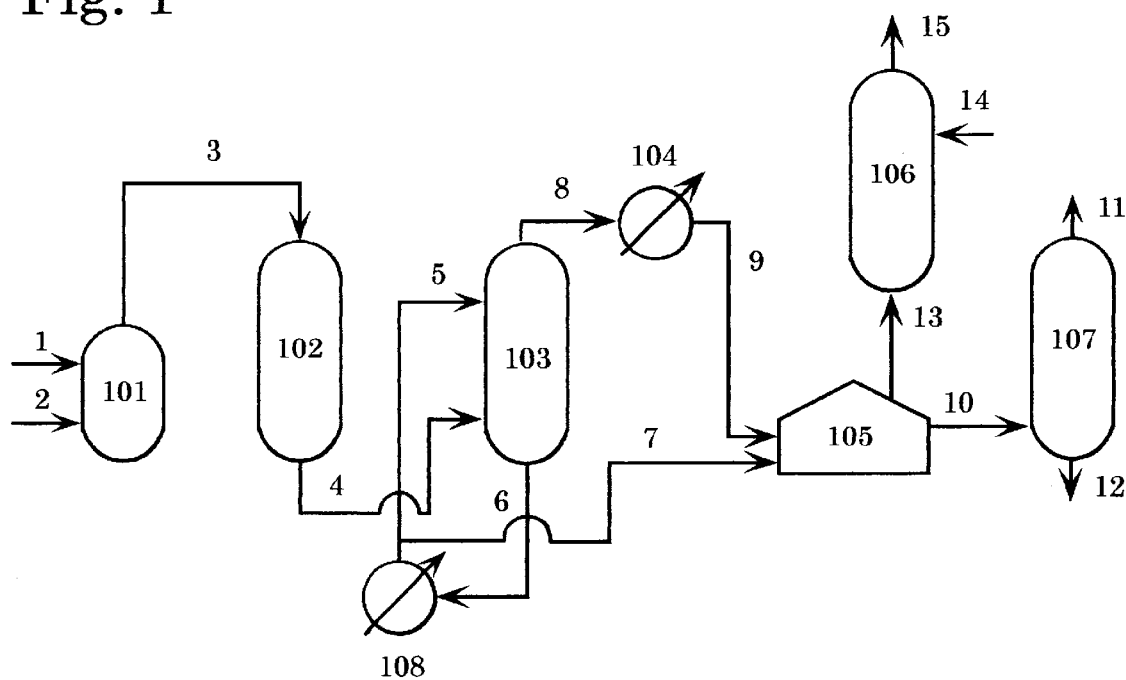
FIG. 1 is a flow sheet illustrating one embodiment of the process (A) of the present invention.

Referring first to FIG. 1, an alkanolamine used as the raw material is fed through a line 1 to an evaporator 101, where it is vaporized. If necessary, the alkanolamine concentration may be controlled by feeding an inert gas (e.g., nitrogen, helium or argon) to evaporator 101 through a line 2, optionally together with other gases (e.g., ammonia, water vapor and hydrogen) used to suppress side reactions. The resulting raw material gas mixture is fed through a line 3 to a reactor 102 packed with a catalyst. After the completion of a dehydration reaction, the reaction gas leaving reactor 102 is composed of an aziridine compound, unreacted alkanolamine, moisture, carbonyl compounds and various amine compounds, in addition to the inert gas used as the raw material gas diluent.

The aforesaid reaction gas is fed through a line 4 to a collection column 103, where it is brought into contact with a collector (usually comprising the same alkanolamine as that used as the raw material) supplied through a line 5. In this process, line 4 is heated with a heater or the like so that the temperature of its outer wall will not be lower than 200° C.

Collection column 103 is usually packed with a packing material but may not be packed. An unabsorbed fraction of the reaction gas is extracted from the top of collection column 103 through a line 8, whereas the collector liquid having the aziridine compound absorbed thereinto is withdrawn from the bottom thereof through a line 6. This collector liquid is introduced into a heat exchanger 108 through line 6 and cooled therein. Thereafter, a portion of the collector liquid is transferred to a storage tank 105 through a line 7, while the remainder is introduced into collection tower 103 through line 5 and used as the collector liquid.

The gas extracted from collection column 103 is condensed by cooling with a heat exchanger 104, and the resulting condensate is transferred to storage tank 105 through a line 9. After the collector liquid from line 7 and the condensate from line 9 are combined and stored in storage tank 105, the combined liquid is fed through a Line 10 to a distillation column 107, where it is purified by distillation to obtain a highly pure aziridine compound product through a line 11. On the other hand, a high-boiling fraction containing unreacted alkanolamine and the like is withdrawn from the bottom of distillation column 107 through a line 12. If necessary, this high-boiling fraction is fed to a recovery step (not shown) for recovering the alkanolamine.

Since the gas discharged from the top of storage tank 105 contains uncollected aziridine compound, this uncollected aziridine compound is recovered by introducing the discharged gas into a collection column 106 through a line 13 and bringing it into contact with a collector supplied through a line 14. The resulting collector liquid is stored in storage tank 105.

Figure 2:
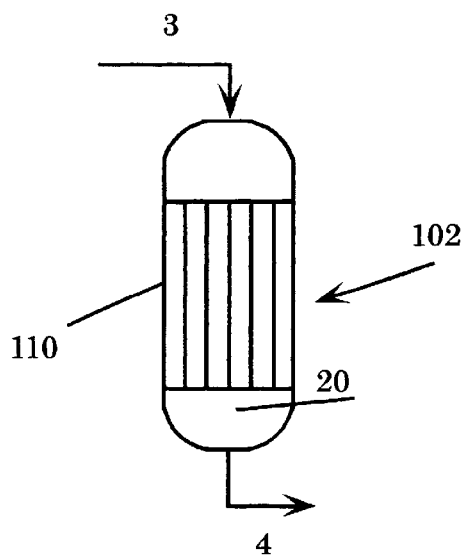
FIG. 2 is a schematic sectional view of a reactor for explaining one exemplary embodiment for bringing the reaction gas into contact with a collector in the process (A) or (B) of the present invention.

Referring now to FIG. 2, the reaction gas leaving a catalyst bed 110 is brought into contact with a collector supplied through a line 20. This collector is usually distributed into reactor 102 with the aid of a sprayer.

The vapor-phase reactions which can be carried out according to the present invention include vapor-phase intramolecular dehydration reactions and vapor-phase intramolecular dealcoholization reactions.

In addition to the above-described reactions for the preparation of aziridine compounds, the vapor-phase intramolecular dehydration reactions include, for example, the reactions for the preparation of cyclic N-vinyl compounds (e.g., vinylpyrrole) by the vapor-phase intramolecular dehydration reaction of cyclic N-(2-hydroxyalkyl) compounds. For the details of these reactions, reference may be made to Japanese Patent Laid-Open No. 208559/'97. Moreover, they also include the reactions for the preparation of vinyl ethers (e.g., methyl vinyl ether and ethyl vinyl ether) by the vapor-phase dehydration reaction of glycol ethers. For the details of these reactions, reference may be made to Japanese Patent Laid-Open No. 143497/'96.

The vapor-phase intramolecular dealcoholization reactions include, for example, the reactions for the preparation of N-vinyl carbamates [e.g., N-vinyl-N-methyl-O-methyl carbamate, N-vinyl-N-ethyl-O-methyl carbamate, N-(1-propenyl)-O-methyl carbamate and N-(1-butenyl)-O-methyl carbamate] by the vapor-phase dealcoholization reaction of N-(1-alkyloxyalkyl) carbamates. For the details of these reactions, reference may be made to Japanese Patent Laid-Open No. 281115/'96.

When a process based on a vapor-phase intramolecular dehydration reaction or dealcoholization reaction as described above is carried out, for example, by using a reactor, a collection column for collecting the desired product present in the reaction gas with the aid of a collector, and a distillation column for distilling the collector liquid to obtain the desired product, the adhesion of tarry matter to piping and the like can be prevented by maintaining at least the piping section extending from the outlet of the reactor to the inlet of the collection column at a temperature which is not lower than 200° C., according to the present invention. Moreover, the adhesion of tarry matter can be more effectively prevented by bringing the reaction gas into contact with a collector prior to its introduction into the collection column (preferably in the neighborhood of the outlet of the catalyst bed within the reactor).

When a process based on a vapor-phase intramolecular dehydration reaction or dealcoholization reaction as described above is carried out, for example, by using a reactor, a cooler for cooling the reaction gas so as to condense it, and a distillation column for distilling the condensate to obtain the desired product, the adhesion of tarry matter to piping and the like can be prevented by bringing the reaction gas into contact with a collector prior to its introduction into the cooler (preferably in the neighborhood of the outlet of the catalyst bed within the reactor), according to the present invention.

For further details of these vapor-phase reactions, reference may be made to the foregoing description given in connection with the preparation of aziridine compounds.

Effects of the Invention

The processes of the present invention make it possible to effectively prevent the adhesion of tarry matter to the inner walls of piping, and the like. Consequently, aziridine compounds can be prepared with industrial advantages, for example, in that it becomes unnecessary to shut down the plant and perform operations for washing off tarry matter. Moreover, various vapor-phase reactions can be carried out with industrial advantages.

EXAMPLES

The present invention is more specifically explained with reference to the following examples.

Example 1

An aziridine compound was prepared according to the flow sheet shown in FIG. 1.

<Preparation of a Catalyst>

While a solution formed by dissolving 900 g of aluminum nitrate (nanohydrate) in 2.4 liters (hereinafter abbreviated as L) of water was being stirred, a solution formed by dissolving 357.6 g of triammonium phosphate in 1.4 L of water was added thereto. The resulting precipitate was collected by filtration, washed with water, and agitated well together with 73.6 g of barium oxide and 100 mL of water. The resulting clayish material was formed into cylindrical pellets having a diameter of about 5 mm and a length of about 5 mm, dried, and then fired at 1,000° C. for 2 hours to obtain a catalyst having the composition $Al_1P_1Ba_{0.2}$ as represented by the atomic ratios of constituent elements except oxygen.

<Reaction Step>

A stainless steel reaction tube having an inner diameter of 25 mm and disposed within reactor 102 was packed with 1 L of the aforesaid catalyst and heated to 420° C. by means of a heating medium. Monoethanolamine was vaporized in evaporator 101 and subjected to a dehydration reaction by passing it through the reaction tube under conditions including a reactor outlet pressure of 133 hPa (100 mmHg) and a space velocity of 400 $h^{-1}$. The reaction gas contained 42.2% by volume of monoethanolamine, 24.7% by volume of ethyleneimine, 27.1% by volume of water, 1.8% by volume of acetaldehyde, and small amounts of ammonia and monoethanolamine dimer.

<Collection Step>

The reaction gas from reactor 102 was conducted through line 4 and introduced into a collection column 103 made of stainless steel and having an inner diameter of 25 mm and a length of 1,000 mm. The lower part of the reactor and the outer wall of line 4 (i.e., the equipment section extending from the outlet of the catalyst bed within the reactor to collection column 103) were maintained at 340° C. by means of an electric heater. To collection column 103, monoethanolamine adjusted to 40° C. was supplied through line 5 at a flow rate of 30 L/h.

When the process was operated for one week and the equipment was then inspected, no adhesion of tarry matter was observed at the outlet of reactor 102 and in line 4, collection column 103 and cooler 104.

Comparative Example 1

An aziridine compound was prepared in the same manner as in Example 1, except that, in the flow sheet of FIG. 1, a double-pipe cooler having an inner diameter of 25 mm was installed in line 4, and the lower part of the reactor and the outer wall of line 4 (i.e., the equipment section extending from the outlet of the catalyst bed within the reactor to collection column 103) were maintained at 150° C.

When the process was operated for one week and the equipment was then inspected, the double-pipe cooler was found to be clogged by the adhesion of tarry matter. Moreover, the adhesion of tarry matter was observed at the outlet of the reactor and in line 4.

What is claimed is:

1. A process for the preparation of aziridine compounds which comprises the step of introducing an alkanolamine into a reactor and forming an aziridine compound by the vapor-phase intramolecular dehydration reaction of the alkanolamine in the presence of a catalyst, and the step of introducing the reaction gas containing the aziridine compound so formed into a collection column and collecting the aziridine compound by contact with a collector, the process being characterized in that at least the piping section extending from the outlet of the reactor to the inlet of the collection column is maintained at a temperature which is not lower than 200° C.

2. A process as claimed in claim 1 wherein the reaction gas is brought into contact with a collector prior to its introduction into the collection column.

3. A process for the preparation of aziridine compounds which comprises the step of introducing an alkanolamine into a reactor and forming an aziridine compound by the vapor-phase intramolecular dehydration reaction of the alkanolamine in the presence of a catalyst, and the step of introducing the reaction gas containing the aziridine compound so formed into a collection column and collecting the aziridine compound by contact with a collector, the process being characterized in that the reaction gas is brought into contact with a collector prior to its introduction into the collection column.

4. A process for the preparation of aziridine compounds which comprises the step of introducing an alkanolamine into a reactor and forming an aziridine compound by the vapor-phase intramolecular dehydration reaction of the alkanolamine in the presence of a catalyst, the step of cooling the reaction gas containing the aziridine compound so formed by means of a cooler so as to condense the reaction gas, and the step of introducing the resulting condensate into a distillation column and distilling it therein to obtain the aziridine compound, the process being characterized in that the reaction gas is brought into contact with a collector prior to its introduction into the cooler.

5. A vapor-phase reaction process comprising a vapor-phase reaction step and a collection step for collecting a desired product present in the reaction gas, or a vapor-phase reaction process comprising a vapor-phase reaction step, a cooling step for condensing the reaction gas, and a distillation step for distilling the resulting condensate, the process being characterized in that at least the piping section extending from the outlet of the reactor to the inlet of the collection column is maintained at a temperature which is not lower than 200° C., or in that the reaction gas is brought into contact with a collector prior to its introduction into the collection column or the cooler.

* * * * *